United States Patent [19]

Vishwakarma et al.

[11] Patent Number: 5,610,000

[45] Date of Patent: Mar. 11, 1997

[54] 2'-HYDROXYPHENYL BENZOTRIAZOLE BASED UV ABSORBING POLYMERS AND PHOTOGRAPHIC ELEMENTS CONTAINING THEM

[75] Inventors: Lal C. Vishwakarma; Hwei-Ling Yau, both of Rochester; Tienteh Chen, Penfield, all of N.Y.

[73] Assignee: Eastman Kodak Company, Rochester, N.Y.

[21] Appl. No.: 454,719

[22] Filed: May 31, 1995

[51] Int. Cl.$^6$ .................................................. G03C 1/815
[52] U.S. Cl. .......................... 430/512; 430/931; 524/91; 526/259; 548/260
[58] Field of Search ........................ 430/512, 931; 524/91; 548/260; 526/259

[56] References Cited

U.S. PATENT DOCUMENTS

| | | | |
|---|---|---|---|
| 3,445,566 | 5/1969 | Skoultchi et al. | 424/47 |
| 3,493,539 | 2/1970 | Skoultchi et al. | 260/47 |
| 3,529,055 | 9/1970 | Skoultchi et al. | 424/47 |
| 4,785,063 | 11/1988 | Slongo et al. | 526/259 |
| 4,943,519 | 7/1990 | Helling et al. | 430/512 |
| 5,099,027 | 3/1992 | Vogi et al. | 548/259 |
| 5,133,745 | 7/1992 | Falcetta et al. | 623/6 |
| 5,372,922 | 12/1994 | Schofield et al. | 430/572 |
| 5,384,235 | 1/1995 | Chen et al. | 430/512 |
| 5,455,152 | 10/1995 | Vishwakarma | 430/512 |

FOREIGN PATENT DOCUMENTS

| | | |
|---|---|---|
| 6-1199738 | 3/1988 | Japan . |
| 6-3205334 | 8/1988 | Japan . |

OTHER PUBLICATIONS

*Research Disclosure*—"Polymerisable UV–absorbers used in photography" by Ciba–Geigy, 32592, p. 357 (May 1991).
*Journal of Macromolecular Science*, Pure Applied Chemistry—"Functional Polymers. LIX. Synthesis and Polymerization of 2(2–Hydroxyphenyl)2H–Benzotriazole–Based Glycidyl Methacrylate Deratives", vol. A30 (9&10), pp. 741–755 (1993).

*Primary Examiner*—Richard L. Schilling
*Attorney, Agent, or Firm*—Edith A. Rice

[57] ABSTRACT

An ultraviolet absorbing polymer, and photographic elements containing such a polymer, which polymer includes units formed from monomers of the structure of formula (II): A photographic element containing an ultraviolet absorbing polymer which includes units formed from monomers of the structure of formula (I):

(I)

(structure shown: benzotriazole with 2'-hydroxyphenyl group, substituent $(L)_p$—$\underset{R_{10}}{\underset{|}{\overset{OR_9}{\overset{|}{C}}}}$—$(L_2)_q$—A)

wherein:
  p and q are, independently, 0 or 1;
  L and $L_2$ are bivalent linking groups;
  $R_9$ is a non-hydrogen group which does not contain any unsaturated carbon-carbon bonds;
  $R_{10}$ is H, alkyl group, aryl group, or heterocyclyl group;
  A is an ethylenically unsaturated polymerizable group; the benzene ring of the benzotriazole and the 2'-hydroxyphenyl ring each may be further substituted or unsubstituted.

28 Claims, 2 Drawing Sheets

—— COMPARATIVE UV POLYMER CP-1
---- INVENTIVE UV POLYMER IP-1

(Graph: DENSITY vs WAVELENGTH, 250–450)

5,610,000

2'-HYDROXYPHENYL BENZOTRIAZOLE BASED UV ABSORBING POLYMERS AND PHOTOGRAPHIC ELEMENTS CONTAINING THEM

FIELD OF THE INVENTION

This invention relates to particular benzotriazole based UV absorbing monomers, and photographic elements containing UV absorbing polymers formed from them.

BACKGROUND

Typical photographic elements use silver halide emulsions (although other light sensitive materials have been known), silver halide having a native sensitivity to ultraviolet radiation. Ultraviolet radiation ("UV") as used in this application means light having a wavelength of 300–400 nm. Such UV sensitivity is usually undesirable in that it produces an image on the photographic element which is not visible to the human eye. Furthermore, the image dyes in the color photographs are known to fade due to action of UV light. Also other organic molecules such as unused color forming couplers in the emulsion layers and optical brighteners in the paper support degrade due to action of UV light and generate undesirable color stains on the finished photographs. Therefore, photographic elements typically contain a UV absorbing compound (sometimes referred to simply as a "UV absorber"). Another function of UV absorbers is to prevent the formation of undesirable patterns caused by electrostatic discharge in silver halide photographic materials. In general, UV absorbers impart light stability to organic molecules in various products which are susceptible to degrade as a result of the action of UV.

Generally, an effective UV absorber should have its peak absorption above a wavelength of 320 nm. The absorption peak may be at a longer wavelength, as long as absorption drops off sufficiently as it approaches the visual range (approximately 400 to 700 nm) so that no visible color is shown by the compound. In addition, to be effective, a UV absorber should have a high extinction coefficient in the desired wavelength range. However, for the most desirable UV protection, the high extinction coefficient should be at those wavelengths sufficiently below the visual range so that the compound should not be visually yellow.

Both conventional and polymeric UV absorbers have been used in photographic elements. Examples of conventional (that is, non-polymeric) UV absorbing compounds are shown by formula (III A) and (III B) below, currently used in color paper as a mixture have the following structures.

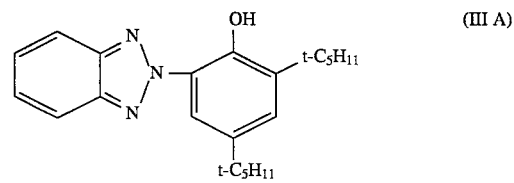

(III A)

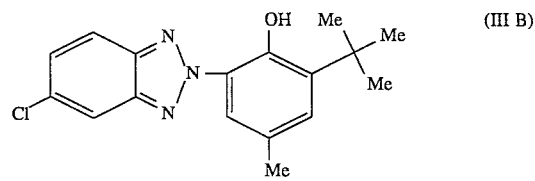

(III B)

It has however, been observed that these compounds and other non-polymeric UV absorbers have a propensity to crystallize out in the coatings. This results in migration of the compound to the surface causing an undesirable blooming effect. Recently, it has been suggested that such compounds are associated with high health risk factors.

It is known that polymer latexes obtained by polymerization of UV absorbing monomers, can be utilized as UV absorbing agents which do not have many of the disadvantages associated with non-polymeric UV absorbers. Photographic performance advantages of UV absorbing polymer latexes have been described, for example in U.S. Pat. No. 5,384,235. That patent discloses a polymerizable 2'-hydroxyphenyl benzotriazole having a 5'-position substituent on the 2'-hydroxyphenyl ring chromophore.

U.S. Pat. No. 3,493,539 discloses synthetic solid polymers (that is, plastic materials) containing UV absorbers of the 2'-hydroxyphenyl benzotriazole type. The described UV absorbers for such use can include those having a 4'-substituent with a secondary alcohol substituent (such an —OH substituent sometimes being referenced herein as an "unblocked" or "unprotected" alcohol group). Similar compounds are described for use in sunscreens, suntanning lotions, optical lenses and similar applications, in U.S. Pat. No. 5,099,027 as well as U.S. Pat. Nos. 5,133,745, 3,529,055, 3,445,566, Journal of Macromolecular Science—Pure Applied Chemistry, Vol. A30 (9& 10), page 741–755 (1993)), and Japanese published patent application (Kokai) JP 63205334. Research Disclosure May, 1991, Item 32592 discloses a polymerizable side chain attached to the 5'-position instead of to 4'-position in the hydroxyphenyl ring. The side chain can contain an unprotected secondary alcohol group. U.S. Pat. No. 5,372,922 discloses similar compounds for use in photographic elements. However, the secondary alcohol group is again unblocked.

It is desirable to provide a UV absorbing polymer and photographic elements containing such a polymer, which polymer contains units formed from a 2'-hydroxyphenyl benzotriazole monomer, and which has good stability in a photographic element environment as well as a high extinction co-efficient and a UV absorption which drops rapidly at or near 400 nm and exhibit little or no yellow coloration.

SUMMARY OF THE INVENTION

It has been discovered that performance characteristics of a UV absorbing polymer containing repeating units of a 2'-hydroxyphenyl benzotriazole with a 4'-substituent having a secondary alcohol group, can be improved by blocking the alcohol group.

Accordingly, the present invention provides UV absorbing polymers, and photographic elements containing them, which polymers include units formed from monomers of the structure of formula (I):

A photographic element containing an ultraviolet absorbing polymer which includes units formed from monomers of the structure of formula (I):

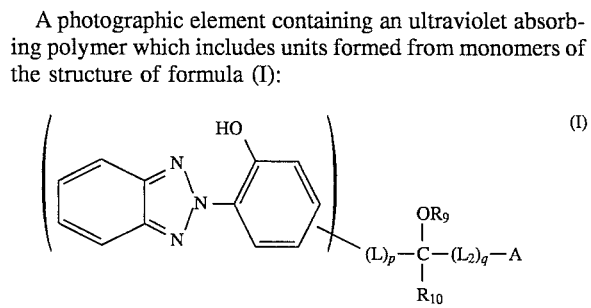

(I)

wherein:

p and q are, independently, 0 or 1;

L and $L_2$ are bivalent linking groups;

$R_9$ is a non-hydrogen group;

$R_{10}$ is H, alkyl group, aryl group, or heterocyclyl group;

A is an ethylenically unsaturated polymerizable group; the benzene ring of the benzotriazole and the 2'-hydroxyphenyl ring each may be further substituted or unsubstituted.

Polymers of formula (I) exhibit, in a photographic element environment, good intrinsic light stability, low fresh blue minimum density ("Dmin"), and good absorption spectral shape. The photographic elements with polymers of formula (I) also have low light-induced yellowing, and good raw stock keeping.

DRAWINGS

EMBODIMENTS OF THE INVENTION

Figure 1:
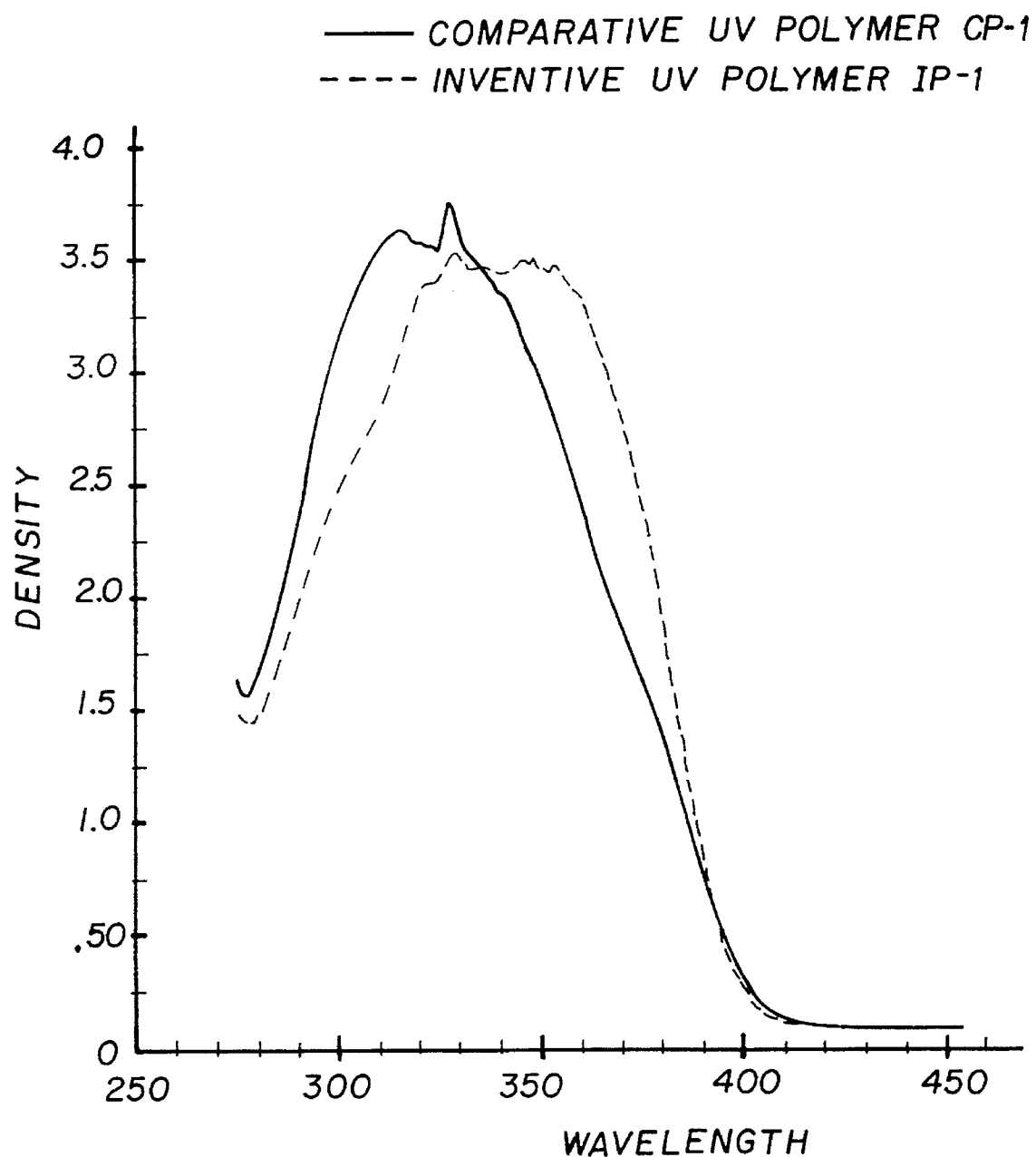
FIG. 1 represents fresh coated absorption spectra of UV absorbing polymers, CP-1 (comparative) and IP-1 (invention).

By reference to "under", "above", "below", "upper", "lower" or the like terms in relation to layer structure of a photographic element, is meant in this application, the relative position in relation to light when the element is exposed in a normal manner. "Above" or "upper" would mean closer to the light source when the element is exposed normally, while "below" or "lower" would mean further from the light source. Since a typical photographic element has the various layers coated on a support, "above" or "upper" would mean further from the support, while "below" or "under" would mean closer to the support. It will also be understood that reference to any broader formula includes reference to compounds with a narrower formula within the broader formula (for example, reference to compounds of formula (I) having particular substituents includes the possibility of compounds of formula (II) having the same substituents unless otherwise indicated).

In reference to "polymers" having units formed from monomers of formula (I) (as already discussed, this includes any compounds falling within formula (I), such as compounds of formula (II), this means that the compound would contain at least 10 (and preferably at least 20 and more preferably at least 50) repeating units of the monomer of formula (I). Typically the polymers would have hundreds (for example, three hundred or more) or several thousand (for example, three thousand or more) repeating units. For a compound to be considered a UV absorbing polymer in the present invention, it should at least absorb somewhere in the 300 to 400 nm region of the spectrum. When reference in this application is made to a substituent "group", this means that the substituent may itself be substituted or unsubstituted (for example "alkyl group" refers to a substituted or unsubstituted alkyl). Generally, unless otherwise specifically stated, substituent groups usable on molecules herein include any groups, whether substituted or unsubstituted, which do not destroy properties necessary for the photographic utility. However, preferably such substituents will not have any unsaturated carbon-carbon bonds since these may cause cross polymerization (that is, preferably only A will contain an unsaturated carbon-carbon bond which will polymerize). It will also be understood throughout this application that reference to a compound of a particular general formula includes those compounds of other more specific formula which specific formula falls within the general formula definition. Examples of substituents on any of the mentioned groups can include known substituents, such as: halogen, for example, chloro, fluoro, bromo, iodo; alkoxy, particularly those "lower alkyl" (that is, with 1 to 6 carbon atoms, for example, methoxy, ethoxy; substituted or unsubstituted alkyl, particularly lower alkyl (for example, methyl, trifluoromethyl); thioalkyl (for example, methylthio or ethylthio), particularly either of those with 1 to 6 carbon atoms; substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); and others known in the art. Alkyl substituents may specifically include "lower alkyl" (that is, having 1–6 carbon atoms), for example, methyl, ethyl, and the like. Further, with regard to any alkyl group or alkylene group, it will be understood that these can be branched or unbranched and include ring structures.

Formula (I) shows that —(L)$_p$ may be appended to any of four available positions on the benzene ring of the benzotriazole moiety, or any of the the four available positions of the benzene ring of the 2'-hydroxyphenyl ring. This includes the possibility that there may be more than 1 of the substituents with —(L)$_p$— attached to the 2'-hydroxyphenyl benzotriazole. However, it is preferred that —(L)$_p$ is appended to the benzene ring of the 2'-hydroxyphenyl so that monomer units of formula (I) are of formula (IA), particularly to the 4' or 5'-positions of that ring, as shown in formula (IB) or (IC) below:

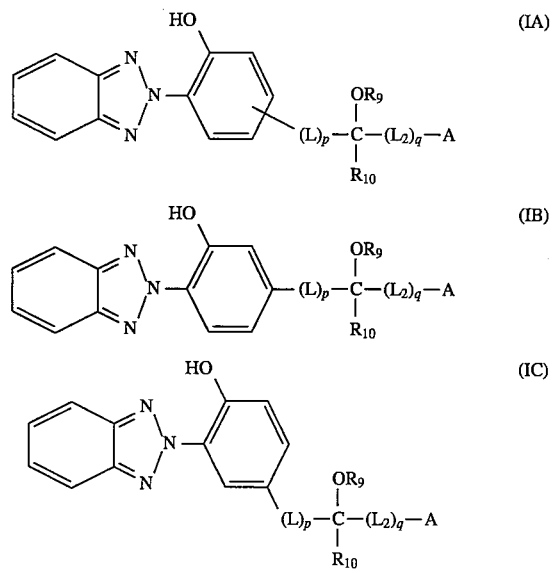

Monomers of formula (I) preferably have L with a formula of —O—(L$_1$)— such that monomers of formula (I) then have the structure of formula (II) below:

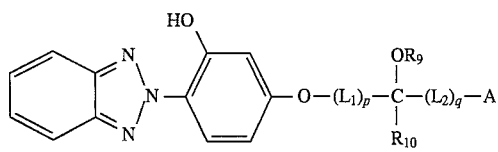

(II)

wherein $L_1$ is a bivalent linking group.

In the above formulae, $R_9$ is preferably an acyl group, alkyl group, aryl group, heterocyclyl group. Examples of $R_9$ include formyl, 1–10 carbon atom alkyl, aryl acyl, carbamyl or alkylsulfonyl (particularly a 1–10 or 1–6 carbon alkyl carbamyl or alkylsulfonyl). Heterocyclyl groups include furyl, thienyl, pyrrolo, pyridyl, imidazolo or pyrazolo.

Substituents on the benzene ring of the benzotriazole or the phenyl ring of the 2'-hydroxyphenyl, where allowed in compounds falling within (I), may for example, independently be 1 to 18 carbon alkyl (or 1 to 6, or 1 to 2 carbon alkyl), aryl (such as 6 to 20 carbon atoms, for example a phenyl group), heteroaryl (such as pyrrolo, furyl or thienyl), aryloxy (such as 6 to 20 carbon atoms) alkoxy (such as 1 to 6 or 1 to 2 carbon alkoxy), cyano, or halogen (for example F or Cl, particularly having Cl on the benzo ring at the 5 and/or 6 position, and/or on the hydroxy substituted phenyl at the 5' position). Substituents for the benzo ring can also include a ring fused thereto, such as a benzo, pyrrolo, furyl or thienyl ring. Any of the alkyl and alkoxy substituents may have from 1 to 5 (or 1 to 2) intervening oxygen, sulfur or nitrogen atoms.

As already described, in formula (I) and (II) L, $L_1$ and $L_2$ are, independently any bivalent linking group. Preferably $L_1$ and $L_2$ are both an alkylene group or alkylene group interrupted by oxygen, nitrogen or sulfur atoms (for example, —O—, —NR— where R is H or an alkyl group such as a lower alky group, or an —SO$_2$—). $L_1$ and $L_2$ may particularly have 1 to 20 carbon atoms, more particularly 4 to 12 carbon atoms, in total, and 1 to 5 heteroatoms selected from O, N or S. It will be understood that $L_1$ and $L_2$ include the possibility of either of them being unbranched linear or branched, or being cyclic. Examples of a linking group for $L_1$ or $L_2$ include —CH$_2$CH$_2$—, —CH$_2$CH$_2$CH$_2$—, —CH$_2$CH$_2$OCH$_2$CH$_2$—, —CH$_2$CH$_2$NHCH$_2$CH$_2$—, —CH$_2$CH(OH)CH$_2$—, —CH$_2$CH$_2$OC(O)CH$_2$CH$_2$—, —CH$_2$CH$_2$NHCOCH$_2$CH$_2$—, —CH$_2$CH$_2$OCH$_2$CHOCH$_2$CH$_2$—, —phenyl—, or cyclohexyl group, or any of the foregoing in which one or more H is replaced by substituents as described above. L could be any of those groups which $L_1$ or $L_2$ represent, although as already described L is preferably —O—$L_1$—.

Monomers of formula (II) are preferably of formula (IIA):

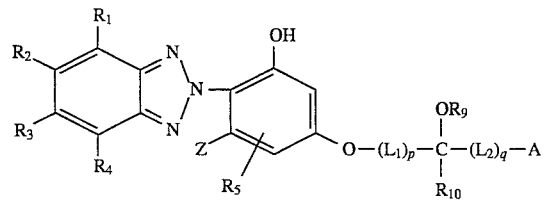

(IIA)

In formula (IIA), p and q are both 1. $R_1$, $R_2$, $R_3$, $R_4$ and $R_5$ are, independently, H, halogen, cyano, carboxy group, carbamoyl group, sulfoxido group, sulfonyl group, sulfonato group, sulfonamido group, alkyl group, alkoxy group, aryl group, heteroaryl group, aryloxy group, or any two or more of $R_1$ through $R_4$ may together form an alicyclic, aromatic or heteroaromatic group. In formula (IIA), the 2'-hydroxyphenyl ring has no further substituents. Z is H or an OH. $L_1$, $L_2$, $R_9$, $R_{10}$, p, q, and A are as defined in connection with formula (IIA).

Monomers of formula (IIA) are more preferably of formula (IIB):

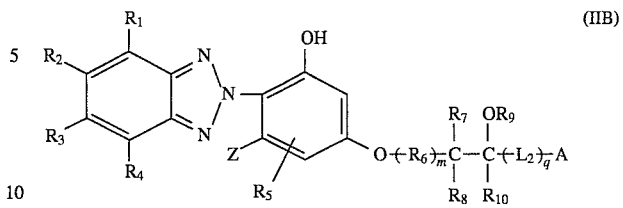

(IIB)

In formula (IIB), $R_1$ through $R_5$, $R_9$, $R_{10}$, Z, $L_2$, q and A are as defined above. m is 0 or 1. $R_7$ and $R_8$ are, independently, H, alkyl group, or together may form an alicyclic or heteroalicyclic ring. $R_6$ is a bivalent linking group and may particularly be any of those linking groups which $L_1$ may represent. Examples of $R_6$ include:

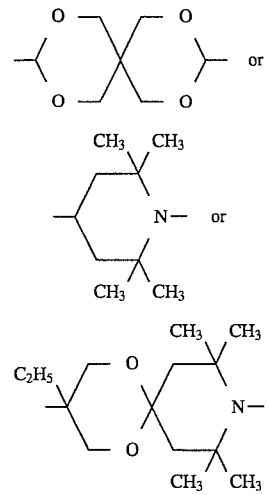

Preferably, in any of the above formula, each of $R_1$ through $R_5$ is, independently, an alkyl group or alkoxy group (particularly either of such groups having 1 to 20 carbon atoms), H or halogen. $R_1$, $R_4$ and $R_5$ are further preferably all H.

Most preferably, formula (II) is chosen such that the units formed from monomers of the structure of formula (II) are units of formula (IIC):

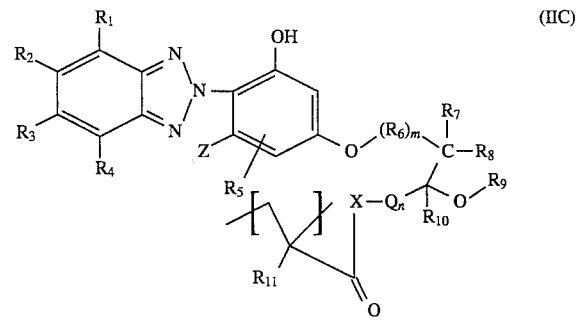

(IIC)

It will be appreciated that formula (IIC) is a type of formula of formula (II) except the formation of the polymer bonds is specifically shown in the square brackets. In formula (IIC), $R_1$ to $R_{10}$, Z, m are as defined above with the preferred ones of them being as indicated above also. n is an integer from 0 to 6 and each Q is a methylene group. X is O or —N(Y)— where Y is H or an alkyl group and $R_{11}$ is H or an alkyl group. Preferably, in formula (IIC), m is O, Q is a methylene group (particularly an unsubstituted methylene), X is O, and $R_{11}$ is H or a 1 to 6 carbon atom alkyl group. More preferably, $R_2$ in formula (IIC) is H and $R_3$ is H, chloro, bromo or fluoro, and $R_7$, $R_8$ and $R_{10}$ are, independently, H or a 1 to 6 carbon atom alkyl group (preferably all of $R_7$, $R_8$ and $R_{10}$ being H).

As to the construction of a photographic element of the present invention, the element has at least one light sensitive layer which is preferably a silver halide emulsion layer. The element additionally preferably has a non-light sensitive layer, with the ultraviolet absorbing polymer being located in the non-light sensitive layer. The non-light sensitive layer containing the ultraviolet absorbing polymer is preferably located above all light sensitive layers.

Examples of monomers of formula (I) are IM-1 through IM-9 shown below. Monomers CM-1 and CM-2 shown below are comparative monomers which are used in the Examples below:

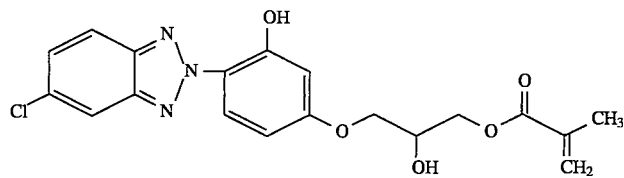

CM-1 (comparison)

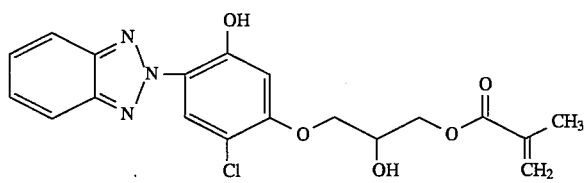

CM-2 (comparison)

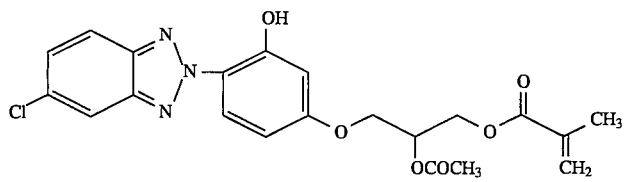

IM-1

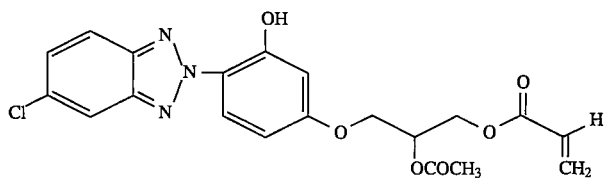

IM-2

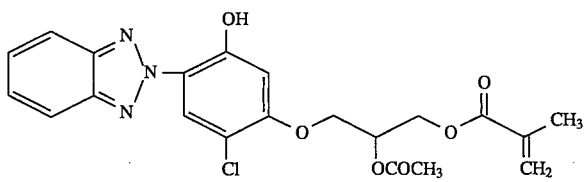

IM-3

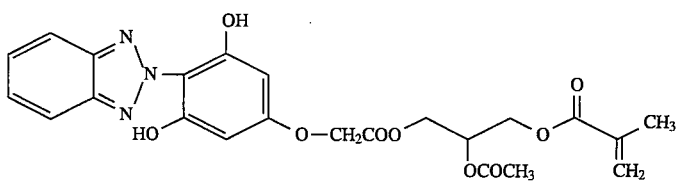

IM-4

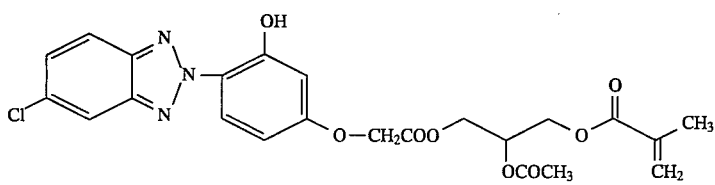

IM-5

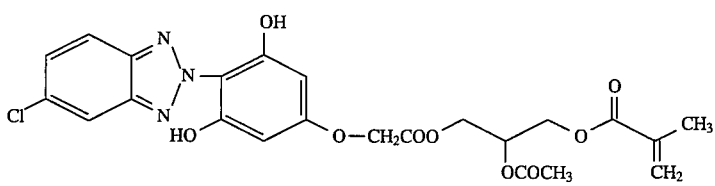

IM-6

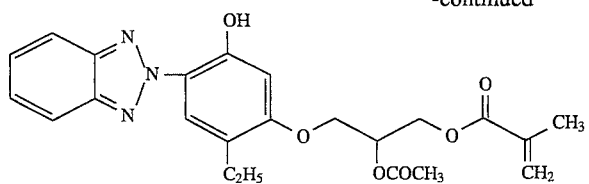
IM-7

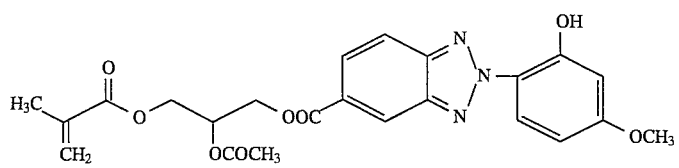
IM-8

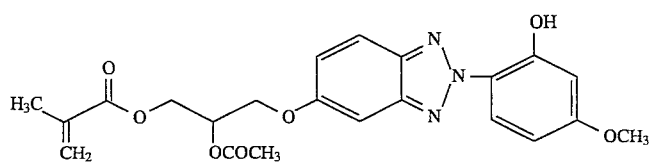
IM-9

The UV absorbing monomers corresponding to the compounds of general formula (II) can be prepared from 2-(2', 4'-dihydroxyphenyl)benzotriazoles (IV).

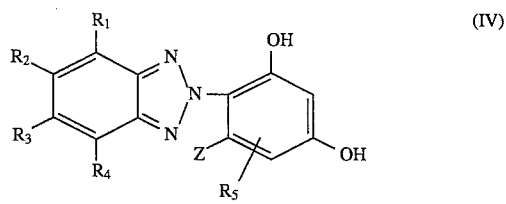

The synthetic procedures for this intermediate are well documented in the art (for example U.S. Pat. No. 3,072,585; European Patent Application 86300416; and U.S. Pat. No. 4,028,331). The intermediate compounds with Z=OH falling under the general formula (IV) could be synthesized by known method (See for example, Y. Jiang et al. *Polymer Bulletin* (Berlin), V. 20(2), p. 169–176 (1988) and *Chemical Abstracts* V. 109, Number 191389). A general procedure for such intermediates is illustrated in Scheme 1 below where the general terms have the previously defined meanings:

Scheme 1

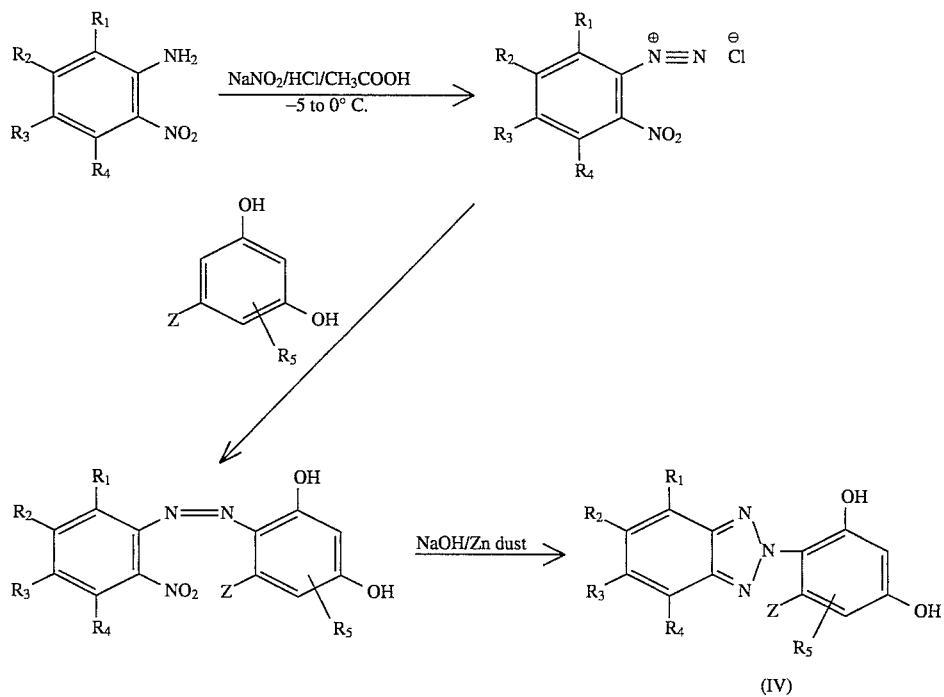

The intermediate compounds of general formula (VI) below could be made by the method known in the prior art (see, for example, M. Minafuji and Y. Nomura, *Japanese Kokai Tokkyo Koho*, JP 03139589, and U.S. Pat. No. 3,214,436).

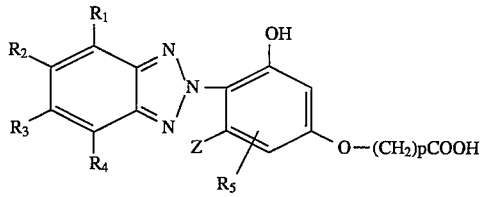

where, p=1–18.

The reactivity of free carboxy group is even better than a phenolic group toward glycidyl acrylate or glycidyl methacrylate. This reaction of (VI) could easily be carried out with glycidyl methacrylate by the method known in the art (see, for example, U.S. Pat. No. 3,493,539). To demonstrate the hydrolytic stability of the carboxy ester group in formula (VII) under our reaction conditions for protecting the sec-OH group we have successfully converted (VII) to novel UV-monomer (VIII). Because (VIII) has protected sec-OH, it is expected to perform photographically better than (VII) as illustrated below.

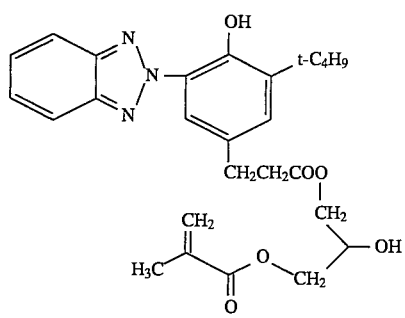

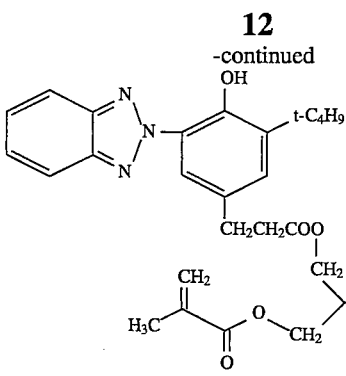

The UV monomers of general formula IX having unprotected secondary OH group were synthesized as shown in Scheme 2:

Scheme 2

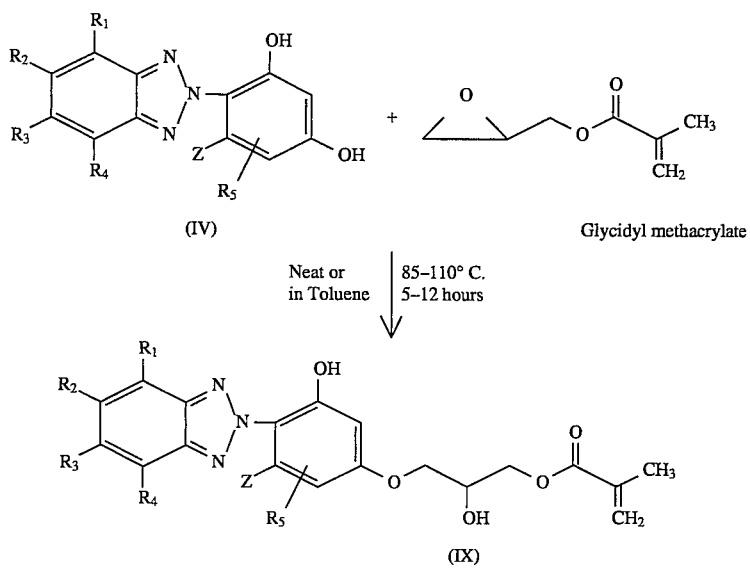

The procedure for making the OH-protected monomers of the present invention (that is, monomers of formula (II)), requires reacting the secondary alcoholic group either with an alkyl tosylate or with an alkyl or aryl group having suitable leaving groups. The most preferred way of protecting the secondary OH group was refluxing the starting monomer under argon gas in simple aliphatic carboxylic acids such as glacial acetic acid in presence of catalytic amount of p-toluenesulfonic acid and an inhibitor such as hydroquinone or azeotropically refluxing equimolar amounts of the two reacting components. Details of such a procedure are given in the Examples below. Other monomers of formula (II) can be made in a similar manner.

Other monomers of formula (I) can be prepared in a manner analogous to that described above for formula (II) compounds. For example, in Scheme I $R_3$ to could be a hydroxy or carboxy, while the 4'-position will be substituted by an alkoxy group. This could be used to provide a compound of formula (I) with the —(L)$_p$— substituent at the 5-position of the benzene ring of the benzotriazole.

The ultraviolet absorbing polymer in the photographic elements of the present invention will have the general formula:

(A)$_x$(B)$_y$

In the above, A is a unit formed from a UV absorbing monomer of a type of formula (I). B is any comonomer (including the possibility that B is another unit formed from a monomer of the type of formula (II) but is different from (A)). x and y are the molar ratio of UV monomer and a comonomer and can be any numbers. However, particularly when B is a comonomer which is not of formula (I) (and more particularly when B is not any UV absorbing monomeric unit) preferably the ratio of y to x is no more than 20:1 (and preferably no more than 10:1 and more preferably no more than 4:1). y may particularly be 0 (in which case the polymer is a homopolymer consisting only of monomeric units formed from the same monomers of formula (II)) but x cannot be 0. When y is not 0, the UV absorbing polymer is a copolymer.

B is a unit formed from any ethylenically unsaturated comonomers, including an acrylic acid, an α-alkylacrylacid (such as methacrylic acid, etc.), an ester or amide derived from an acrylic acid or methacrylic acid(for example, acrylamide, methacrylamide, n-butylacrylamide, t-butylacrylamide, diacetone acrylamide, methyl acrylate, ethyl acrylate, n-propylacrylate, n-butyl acrylate, t-butyl acrylate, isobutyl acrylate, 2-ethylhexyl acrylate, n-octyl acrylate, lauryl acrylate, 2-ethoxyethyl acrylate, 2-methoxyethyl acrylate,methyl methacrylate, ethyl methacrylate, n-butyl methacrylate, β-hydroxyl methacrylate, etc.), a vinyl ester(for example, vinyl acetate, vinyl propionate, vinyl laurate, etc.), acrylonitrile, methacrylonitrile, an aromatic vinyl compound (for example, styrene and a derivative thereof, for example, vinyl toluene, divinylbenzene, vinyl acetophenone, sulfostyrene, etc.), itaconic acid, citraconic acid, crotonic acid, vinylidene chloride, a vinyl alkyl ether(for example, vinyl ethyl ether, etc.), an ester of maleic acid, N-vinyl-2-pyrrolidone, N-vinylpyridine, 2- or 4-vinylpyridine, etc., an sulfonic acid containing monomers, (for example, acrylamido-2,2'-dimethyl-propane sulfonic acid, 2-sulfoethyl methacrylate, 3-sulfopropyl methacrylate, and the like).

Of the monomers from which B is formed, an ester of acrylic acid, an ester of methacrylic acid, and an aromatic vinyl compounds are particularly preferred.

Two or more of the above-described comonomers which form B, can be used together, for example, a combination of butyl acrylate and acrylamido-2,2'-dimethyl propane sulfonic acid.

Two or more of the UV absorbing monomers can be copolymerized together, for example, a combination of CM-1 with IM-1 or with other UV absorbing monomers described in the prior art. Particularly, a copolymer may contain units of the formula:

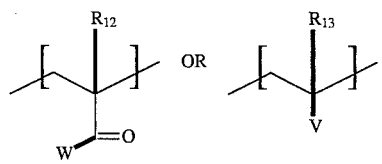

wherein: W is an amino group (such as one with one or two further alkyl group substituents, particularly lower alkyl groups), alkoxy group, or phenoxy group; V is a substituted or unsubstituted phenyl; and $R_{12}$ and $R_{13}$ are H or a substituted or unsubstituted 1 to 6 carbon atom alkyl.

Examples of suitable polymers of the present invention are IP-1 and IP-2 below (structures of comparative polymers CP-1 and CP-2 are also provided below):

IP-1 (invention)

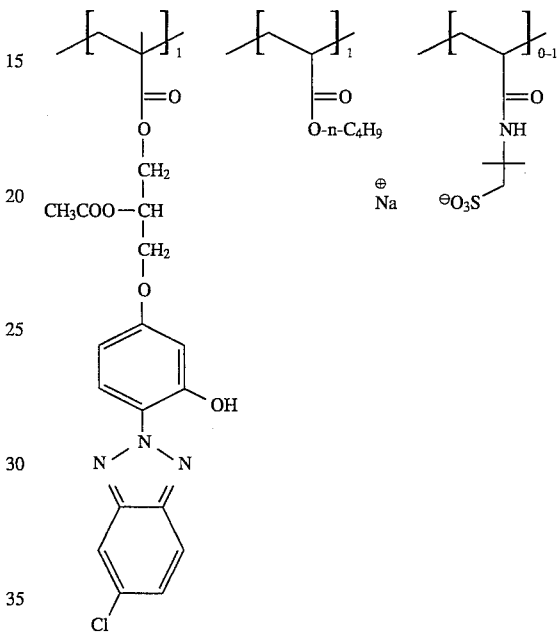

IP-2 (invention)

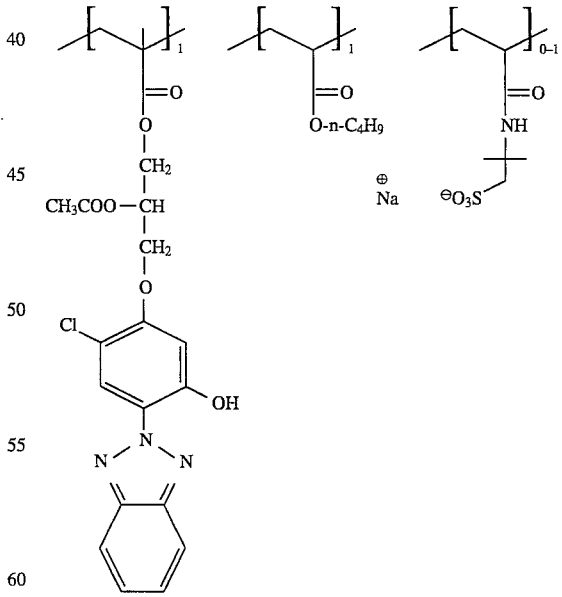

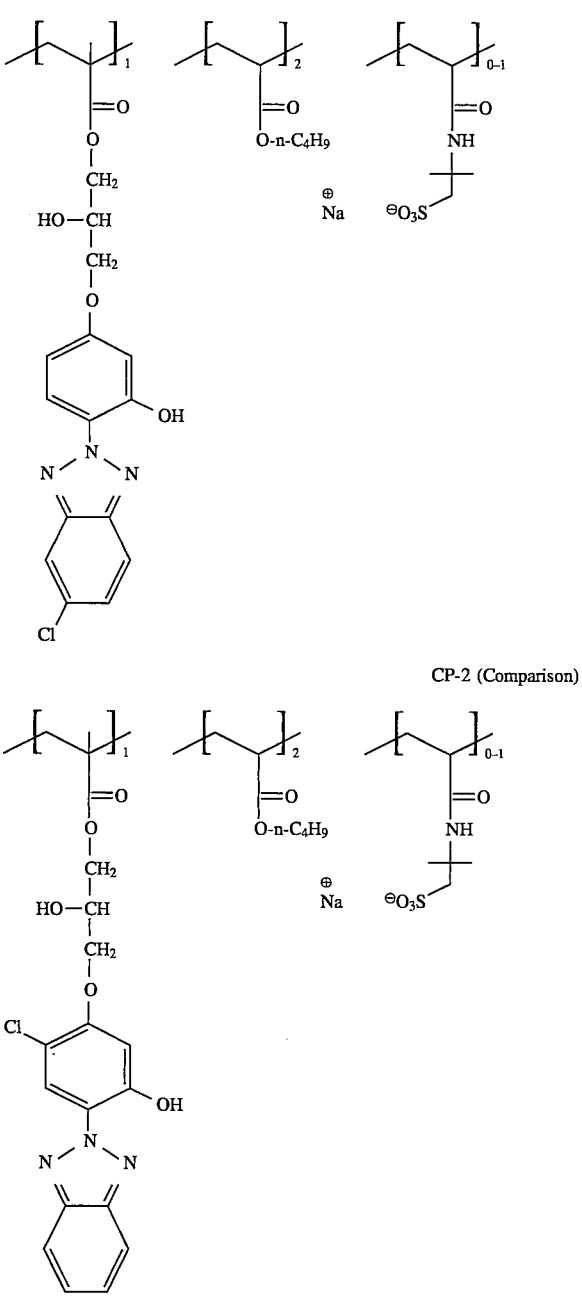

CP-1 (Comparison)

CP-2 (Comparison)

Other examples of UV absorbing polymers of the present invention are listed in Table A below, which polymers contain repeating units formed from UV absorbing monomers of the following structure (M):

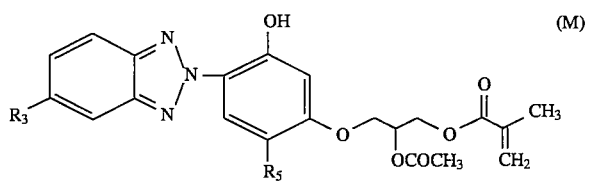

TABLE A

| Polymer I.D. | Substituent ($R_3$ or $R_5$)* | Compositions | Molar Ratio |
|---|---|---|---|
| IP-3 | 5-Cl | IM-1:Ba:NaAMPS | 1:2:0.1 |
| IP-4 | 5-Cl | IM-1:Ea:NaAMPS | 1:1:0.1 |
| IP-5 | 5-Cl | IM-1:Ea:NaAMPS | 1:2:0.1 |
| IP-6 | 5-Cl | IM-1:EEa:NaAMPS | 1:1:0.1 |
| IP-7 | 5-Cl | IM-1:EEa:NaAMPS | 1:2:0.1 |
| IP-8 | 5'-Cl | IM-3:Ba:NaAMPS | 1:2:0.1 |
| IP-9 | 5'-Cl | IM-3:Ea:NaAMPS | 1:1:0.1 |
| IP-10 | 5'-Cl | IM-3:Ea:NaAMPS | 1:2:0.1 |
| IP-11 | 5'-Cl | IM-3:EEa:NaAMPS | 1:1:0.1 |
| IP-12 | 5'-Cl | IM-3:EEa:NaAMPS | 1:2:0.1 |
| IP-13 | 5-MeO | M:Ba:NaAMPS | 1:1:0.1 |
| IP-14 | 5-MeO | M:Ba:NaAMPS | 1:2:0.1 |
| IP-15 | 5-MeO | M:Ea:NaAMPS | 1:1:0.1 |
| IP-16 | 5-MeO | M:Ea:NaAMPS | 1:2:0.1 |
| IP-17 | 5-MeO | M:EEa:NaAMPS | 1:1:0.1 |
| IP-18 | 5-MeO | M:EEa:NaAMPS | 1:2:0.1 |
| IP-19 | 5-Me | M:Ba:NaAMPS | 1:1:0.1 |
| IP-20 | 5-Me | M:Ba:NaAMPS | 1:2:0.1 |
| IP-21 | 5-Me | M:Ea:NaAMPS | 1:1:0.1 |
| IP-22 | 5-Me | M:Ea:NaAMPS | 1:2:0.1 |
| IP-23 | 5-Me | M:EEa:NaAMPS | 1:1:0.1 |
| IP-24 | 5-Me | M:EEa:NaAMPS | 1:2:0.1 |
| IP-25 | 5'-Et | M:Ba:NaAMPS | 1:1:0.1 |
| IP-26 | 5'-Et | M:Ba:NaAMPS | 1:2:0.1 |
| IP-27 | 5'-Et | M:Ea:NaAMPS | 1:1:0.1 |
| IP-28 | 5'-Et | M:Ea:NaAMPS | 1:2:0.1 |
| IP-29 | 5'-Et | M:EEa:NaAMPS | 1:1:0.1 |
| IP-30 | 5'-Et | M:EEa:NaAMPS | 1:2:0.1 |
| IP-31 | 5'-Me | M:Ba:NaAMPS | 1:1:0.1 |
| IP-32 | 5'-Me | M:Ba:NaAMPS | 1:2:0.1 |
| IP-33 | 5'-Me | M:Ea:NaAMPS | 1:1:0.1 |
| IP-34 | 5'-Me | M:Ea:NaAMPS | 1:2:0.1 |
| IP-35 | 5'-Me | M:EEa:NaAMPS | 1:1:0.1 |
| IP-36 | 5'-Me | M:EEa:NaAMPS | 1:2:0.1 | where, M is a UV absorbing monomer; Ba = BUtyl acrylate; Ea = Ethyl acrylate; EEa = 2-Ethoxyethyl acrylate; NaAMPS = Sodium acrylamido-2-methyl-1-propane sulfonic acid.
*When the substituent is indicated as "5-" this means it is on the 5-position of the benzene ring of the benzotriazole group; when the substituent is "5'-" this means it is on the 5'-position of the 2'-hydroxyphenyl ring.

All of the above formulas are based on molar ratios of monomers.

The polymer latexes are preferably prepared by emulsion polymerization. Emulsion polymerization is well known in the art and is described, for example, in F. A. Bovey, *Emulsion Polymerization*, issued by Interscience Publishers Inc. New York, 1955. Examples of the chemical initiators which may be used include a thermally decomposable initiator, for example, a persulfate (such as ammonium persulfate, potassium persulfate, etc), hydrogen peroxide, 4,4'-azobis(4-cyanovaleric acid), and redox initiators such as hydrogen peroxide-iron(II) salt, potassium persulfate-sodium hydrogensulfate, cerium salt-alcohol, etc. Emulsifiers which may be used in the emulsion polymerization include soap, a sulfonate(for example, sodium N-methyl-N-oleoyltaurate, etc.), a sulfate( for example, sodium dodecyl sulfate, etc.), a cationic compound(for example, hexadecyl trimethylammonium bromide, etc.), an amphoteric compound and a high molecular weight protective colloid(for example, polyvinyl alcohol, polyacrylic acid, gelatin, etc.). Specific examples and functions of the emulsifiers are described in *Belgische Chemische Industrie*, Vol.28, pages 16–20(1963).

Emulsion polymerization of solid water-insoluble UV absorbing monomer is usually carried out in an aqueous system or a water/organic solvent system. Organic solvents which can be used are preferably those which have high water miscibility, are substantially inert to the monomers to be used, and do not interrupt usual reactions in free radical addition polymerization. Preferred examples include a lower alcohol having from 1 to 4 carbon atoms (for example, methanol, ethanol, isopropanol, etc.), a ketone(for example, acetone, etc.), a cyclic ether (for example, tetrahydrofuran, etc.), a nitrile (for example, acetonitrile,etc.), an amide (for example, N,N-dimethylforamide, etc.), a sulfoxide (for example, dimethylsulfoxide), and the like. This method is the most direct way of preparing a polymer latex as described in U.S. Pat. Nos. 4,464,462; 4,455,368 and European Patent publication 0,190,003 (1991).

High boiling organic solvents (so-called coupler solvent) can also be added to modify the physical properties of the photographic materials. The loading of high boiling organic solvents into polymer latex was described in the following publications: U.S. Pat. No. 4,199,363, U.S. Pat. No. 4,203,716, U.S. Pat. Nos. 4,214,047, 4,247,627, 4,497,929, and U.S. Pat. No. 4,608,424.

As to the method of loading the high boiling point organic solvent in the polymer latex, "loading" a polymer latex is generally described in U.S. Pat. No. 4,199,363 for example. There are several methods of loading the high boiling point solvents into the polymer latex. First, an aqueous dispersion of a high boiling point solvent (or mixture of such solvents) is prepared by the conventional colloid mill process in the presence of gelatin. This dispersion is then blended with the polymer latex such that the weight ratio of high boiling, water immiscible organic solvent to polymer latex is between 0.1 to 5.0 (that is, 0.1/1 to 5.0/1 of solvent/polymer latex), and more preferably between 0.2 to 3.0 (that is, 0.2/1 to 3.0/1 of solvent/polymer latex).

In a second method of loading the polymer latex, the high boiling point solvent is loaded into the polymeric UV absorbing agent in the presence of low boiling organic solvents, such as methanol or acetone. The auxiliary solvent is then evaporated with a rotary evaporator. The same weight ratios of high boiling, water immiscible organic solvent can be used as in the above method.

Loading of a polymer latex is also described, for example, in U.S. Pat. Nos. 4,203,716, 4,214,047, 4,247,627, 4,497,929 and U.S. Pat. No. 4,608,424.

Conventional (that is, monomeric) UV absorbers can also be loaded into the UV absorbing polymer latexes of the photographic elements of the present invention to alter their photographic performance. Examples of such conventional UV absorbing agents which can be used include: 2-(2-hydroxy-5-methylphenyl)-2H-benzotriazole, 2-(2-hydroxy-3,5-di-tert-butylphenyl)-2H-benzotriazole, 2-(2-hydroxy-3-tert-butyl-5-methylphenyl)-2H-benzotriazole, 2-(2-hydroxy-3,5-di-tert-butylphenyl)-5-chloro-2H-benzotriazole, 2-(2-hydroxy-3,5-di-tert-amylphenyl)-2H-benzotriazole, 2-(2-hydroxy-3,5-di(1,1-dimethylbenzyl)-phenyl)-2H-benzotriazole, 2-(2-hydroxy-5-tert-octylphenyl)-2H-benzotriazole. Other types of UV absorbing agents include p-hydroxybenzoates, phenylesters of benzoic acid, salicylanilides and oxanilides, diketones, benzylidene malonate, esters of α-cyano-β-phenylcinnamic acid, and organic metal photostabilizers, and others, as described in J. F. Rabek, *Photostabilization of Polymers, Principles and Applications*, Elsevier Science Publishers LTD, England, page 202–278 (1990).

A dispersion of a polymer of the present invention is incorporated into the photographic element (typically into a gelatin gel thereof) in an amount of between 0.2 $g/m^2$ to 10 $g/m^2$, and more preferably between 0.5 $g/m^2$ to 5.0 $g/m^2$. Furthermore, the weight ratio of high boiling, water immiscible organic solvent, when present, to polymer latex is preferably between 0.1 to 5.0 (that is, 0.1/1 to 5.0/1 of solvent/polymer latex), and more preferably between 0.2 to 3.0 (that is, 0.2/1 to 3.0/1 of solvent/polymer latex).

The polymer of the present invention is provided in any one or more of the layers (for example, a hydrophilic colloid layer) of a photographic light-sensitive material (preferably a silver halide photographic light-sensitive material), such as a surface protective layer, an intermediate layer or a silver halide emulsion layer, and the like. For example, in photographic paper the UV absorbing polymer latex may be positioned above and/or below the red sensitive layer (preferably above and adjacent to it), the red sensitive layer typically being the uppermost light sensitive layer in color paper, or even completely or partially within the red sensitive layer.

The photographic elements made by the method of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one greensensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support).

Photographic elements of the present invention may also usefully include a magnetic recording material as described in *Research Disclosure*, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support) and the reverse order on a reflective support being typical.

The present invention also contemplates the use of photographic elements of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

In the following discussion of suitable materials for use in elements of this invention, reference will be made to *Research Disclosure*, September 1994, Number 365, Item 36544, which will be identified hereafter by the term "Research Disclosure I." The Sections hereafter referred to are Sections of the Research Disclosure I unless otherwise indicated. All Research Disclosures referenced are published by Kenneth Mason Publications, Ltd., Dudley Annex, 12a North Street, Emsworth, Hampshire P010 7DQ, ENGLAND. The foreoging references and all other references cited in this application, are incorporated herein by reference.

The silver halide emulsions employed in the photographic elements of the present invention may be negative-working, such as surface-sensitive emulsions or unfogged internal latent image forming emulsions, or positive working emulsions of internal latent image forming emulsions (that are either fogged in the element or fogged during processing). Suitable emulsions and their preparation as well as methods of chemical and spectral sensitization are described in Sections I through V. Color materials and development modifiers are described in Sections V through XX. Vehicles which can be used in the photographic elements are described in Section II, and various additives such as brighteners, antifoggants, stabilizers, light absorbing and scattering materials, hardeners, coating aids, plasticizers, lubricants and matting agents are described, for example, in Sections VI through XIII. Manufacturing methods are described in all of the sections, layer arrangements particularly in in Section XI, exposure alternatives in Section XVI, and processing methods and agents in Sections XIX and XX.

With negative working silver halide a negative image can be formed. Optionally a positive (or reversal) image can be formed although a negative image is typically first formed.

The photographic elements of the present invention may also use colored couplers (e.g. to adjust levels of interlayer correction) and masking couplers such as those described in EP 213 490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193 389; EP 301 477; U.S. Pat. Nos. 4,163,669; 4,865,956; and 4,923,784 are particularly useful. Also contemplated is the use of nucleating agents, development accelerators or their precursors (U.K. Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil-in-water dispersions, latex dispersions or as solid particle dispersions. Additionally, they may be used with "smearing" couplers (e.g. as described in U.S. Pat. No. 4,366,237; EP 096 570; 4,420,556; and U.S. Pat. No. 4,543, 323.) Also, the couplers may be blocked or coated in protected form as described, for example, in Japanese Application 61/258,249 or U.S. Pat. No. 5,019,492.

The photographic elements may further contain other image-modifying compounds such as "Developer Inhibitor-Releasing" compounds (DIR's). Useful additional DIR's for elements of the present invention, are known in the art and examples are described in U.S. Pat. Nos. 3,137,578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4,126,459; 4,149,886; 4,150,228; 4,211, 562; 4,248,962; 4,259,437; 4,362,878; 4,409,323; 4,477, 563; 4,782,012; 4,962,018; 4,500,634; 4,579,816; 4,607, 004; 4,618,571; 4,678,739; 4,746,600; 4,746,601; 4,791, 049; 4,857,447; 4,865,959; 4,880,342; 4,886,736; 4,937, 179; 4,946,767; 4,948,716; 4,952,485; 4,956,269; 4,959, 299; 4,966,835; 4,985,336 as well as in patent publications GB 1,560,240; GB 2,007,662; GB 2,032,914; GB 2,099, 167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in Photographic Science and Engineering, Vol. 13, p. 174 (1969), incorporated herein by reference.

It is also contemplated that the concepts of the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. Nos. 4,346,165; 4,540,653 and 4,906, 559); with ballasted chelating agents such as those in U.S. Pat. No. 4,994,359 to reduce sensitivity to polyvalent cations such as calcium; and with stain reducing compounds such as described in U.S. Pat. No. 5,068,171 and U.S. Pat. No. 5,096,805. Other compounds useful in the elements of the invention are disclosed in Japanese Published Applications 83-09,959; 83-62,586; 90-072,629, 90-072,630; 90-072, 632; 90-072,633; 90-072,634; 90-077,822; 90-078,229; 90-078,230; 90-079,336; 90-079,338; 90-079,690; 90- 079, 691; 90-080,487; 90-080,489; 90-080,490; 90-080,491; 90-080,492; 90-080,494; 90-085,928; 90-086,669; 90-086, 670; 90-087,361; 90-087,362; 90-087,363; 90-087,364; 90-088,096; 90-088,097; 90-093,662; 90-093,663; 90-093, 664; 90-093,665; 90-093,666; 90-093,668; 90-094,055; 90-094,056; 90-101,937; 90-103,409; 90-151,577.

The silver halide used in the photographic elements may be silver iodobromide, silver bromide, silver chloride, silver chlorobromide, silver chloroiodobromide, and the like. For example, the silver halide used in the photographic elements of the present invention may contain at least 90% silver chloride or more (for example, at least 95%, 98%, 99% or 100% silver chloride). In the case of such high chloride silver halide emulsions, some silver bromide may be present but typically substantially no silver iodide. Substantially no silver iodide means the iodide concentration would be no more than 1%, and preferably less than 0.5 or 0.1%. In particular, in such a case the possibility is also contemplated that the silver chloride could be treated with a bromide source to increase its sensitivity, although the bulk concentration of bromide in the resulting emulsion will typically be no more than about 2 to 2.5% and preferably between about 0.6 to 1.2% (the remainder being silver chloride). The foregoing % figures are mole %.

The type of silver halide grains preferably include polymorphic, cubic, and octahedral. The grain size of the silver halide may have any distribution known to be useful in photographic compositions, and may be either polydipersed or monodispersed.

Tabular grain silver halide emulsions may also be used. Tabular grains are those with two parallel major faces each clearly larger than any remaining grain face and tabular grain emulsions are those in which the tabular grains account for at least 30 percent, more typically at least 50 percent, preferably >70 percent and optimally >90 percent of total grain projected area. The tabular grains can account for substantially all (>97 percent) of total grain projected area. The tabular grain emulsions can be high aspect ratio tabular grain emulsions-i.e., ECD/t >8, where ECD is the diameter of a circle having an area equal to grain projected area and t is tabular grain thickness; intermediate aspect ratio tabular grain emulsions—i.e., ECD/t=5 to 8; or low aspect ratio tabular grain emulsions—i.e., ECD/t=2 to 5. The emulsions typically exhibit high tabularity (T), where T (i.e., ECD/$t^2$)>25 and ECD and t are both measured in micrometers (μm). The tabular grains can be of any thickness compatible with achieving an aim average aspect ratio and/or average tabularity of the tabular grain emulsion. Preferably the tabular grains satisfying projected area requirements are those having thicknesses of <0.3 μm, thin (<0.2 μm) tabular grains being specifically preferred and ultrathin (<0.07 μm) tabular grains being contemplated for maximum tabular grain performance enhancements. When the native blue absorption of iodohalide tabular grains is relied upon for blue speed, thicker tabular grains, typically up to 0.5 μm in thickness, are contemplated.

High iodide tabular grain emulsions are illustrated by House U.S. Pat. No. 4,490,458, Maskasky U.S. Pat. No. 4,459,353 and Yagi et al EPO 0,410,410.

Tabular grains formed of silver halide(s) that form a face centered cubic (rock salt type) crystal lattice structure can have either {100} or {111} major faces. Emulsions containing {111} major face tabular grains, including those with controlled grain dispersities, halide distributions, twin plane spacing, edge structures and grain dislocations as well as adsorbed {111} grain face stabilizers, are illustrated in those references cited in *Research Disclosure I*, Section I.B.(3) (page 503).

The silver halide grains to be used in the invention may be prepared according to methods known in the art, such as those described in *Research Disclosure I* and James, *The Theory of the Photoqraphic Process*. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in *Research Disclosure I* and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30° to 80° C., as described in *Research Disclosure I*, Section IV (pages 510–511) and the references cited therein.

The silver halide may be sensitized by sensitizing dyes by any method known in the art, such as described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dyes may, for example, be added as a solution in water or an alocohol. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in *Research Disclosure I*, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic elements comprising the composition of the invention can be processed in any of a number of well-known photographic processes utilizing any of a number of well-known processing compositions, described, for example, in *Research Disclosure I*, or in T. H. James, editor, *The Theory of the Photographic Process*, 4th Edition, Macmillan, N.Y., 1977. In the case of processing a negative working element, the element is treated with a color developer (that is one which will form the colored image dyes with the color couplers), and then with a oxidizer and a solvent to remove silver and silver halide. In the case of processing a reversal color element, the element is first treated with a black and white developer (that is, a developer which does not form colored dyes with the coupler compounds) followed by a treatment to fog silver halide (usually chemical fogging or light fogging), followed by treatment with a color developer. Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(β-methanesulfonamido) ethylaniline sesquisulfate hydrate, 4-amino-3-methyl-N-ethyl-N-(β-hydroxyethyl)aniline sulfate, 4-amino-3-β-(methanesulfonamido)ethyl-N,N-diethylaniline hydrochloride and 4-amino-N-ethyl-N-(2-methoxyethyl)-m-toluidine dip toluene sulfonic acid.

Development is followed by bleach-fixing, to remove silver or silver halide, washing and drying.

The present invention will be further described in the examples below.

Synthesis of UVmonomer IM-1

In a 500 mL round-bottom flask, a mixture of UVmonomer CM-1 (10.00 g, 0.0248 mole), 200 mL of glacial acetic acid, 1.00 g of p-toluenesulfonic acid, and 0.10 g of 2,6-di-t-butyl-4-methyl phenol was refluxed on a heating mantle for 6 hours. The flask was cooled down to room temperature. A small amount (0.88 g) of insoluble solid material was filtered off. The filtrate was poured into 500 mL of cold water. The precipitated white solid was collected on a sintered glass funnel and was washed with cold water (2×150 mL) to remove residual acetic acid and catalyst. It was air-dried and further purified by silica gel flash column chromatography eluting with dichloromethane. Removal of solvent gave 8.0 g of pure product. Its FD Mass Spectrum showed $M^+$ at m/e 445. Its UV-VIS in methanol had an absorption $\lambda_{max}$ at 344 nm with molar extinction coefficient of 24,300. Its elemental analysis for $C_{21}H_{20}Cl_1N_3O_6$ showed calculated: C, 56.57; H, 4.52; N, 9.42. Found: C, 56.67; H, 4.46; N, 9.43.

Synthesis of UV monomer IM-3

In a 500 mL round-bottom flask, a mixture of UV monomer CM-2 (11.80 g, 0.029 mole), 300 mL of glacial acetic acid, 1.40 g of p-toluenesulfonic acid, and 0.05 g of 2,6-di-t-butyl-4-methyl phenol was refluxed on a heating mantle for 16 hours. The flask was cooled down to room temperature. Solvent was removed completely on a rotary evaporator. Pasty residual material was triturated with 100 mL cold water and decanted off. The residual pasty material was then extracted with 300 mL of dichloromethane. It was washed with 100 mL of brine. It was dried over anhydrous sodium sulfate (15 g) which was filtered off. The filtrate was mixed with 100 g of silica gel and dichloromethane was removed on rotary evaporator. Flash chromatography column of this dry powder gave 12 g of pure product as white solid material. Its FD Mass 5 Spectrum showed $M^+$ at m/e 445. Its UV-VIS in methanol had an absorption $\lambda_{max}$ at 342 nm with molar extinction coefficient of 22,500. Its elemental analysis for $C_{21}H_{20}Cl_1N_3O_6$ showed calculated: C, 56.57; H, 4.52; N, 9.42. Found: C, 56.62; H, 4.58; N, 9.46.

The following examples illustrate a general preparative procedure for all the UV absorbing polymers of general formula (II). The comparative polymers from all the UVmonomers of general formula (IX) were also made analogously. The comparative compositions of this invention are identified as C-1, CP-1 and CP-2. The composition C-1 is conventional dispersion of Compounds (III-A, Tinuvin 328) and (III-B, Tinuvin 326) whereas the comparative examples CP-1 and CP-2 are latexes of copolymers which were made from corresponding UV monomers CM-1 and CM-2 of general formula (IX). These comparative UVmonomers bear secondary alcoholic group in their polymerizable side chains.

Synthesis of polymer IP-1

30 g of deionized water, 0.73 g of sodium N-methyl-N-oleyltaurate (Igepon T-33), and 3 mL of N,N-dimethylformamide were mixed in a 0.5 L 4-neck round bottom flask equipped with a mechanical stirrer, nitrogen inlet, and a condenser. The flask was immersed in a constant temperature bath at 80° C. and heated for 30 mins with nitrogen purging through. 0.9 g of 10% sodium persulfate was added. 5 mins later, monomer solution comprising 6.69 g of UV monomer IM-1 (0.015 mole), 1.923 g(0.015 mole) of butyl acrylate, and 60 mL of N,N-dimethylformamide was feeded into reactor over four hours. Cofeed solution comprising 0.73 g of Igepon T-33, 0.9 g of 10% sodium persulfate, 0.59 g(0.0015 mole) of sodium acrylamido-2-methyl-2-propane sulfonic acid, 0.9 g of sodium bicarbonate and 180 mL water was pumped into the reactor together concurrently. The polymerization was continued for overnight. The latex was cooled, filtered, dialyzed, and concentrated to 3.84% solid with Amicon's Ultrafiltration unit. The Z-average particle size measured by Malvern's Autosizer IIC was 75 nm. The elemental analysis confirmed the composition.

Synthesis of polymer IP-2

30 g of deionized water, 0.73 g of sodium N-methyl-N-oleyltaurate (Igepon T-33), and 3 mL of N,N-dimethylforamide were mixed in a 0.5L 4-neck round bottom flask equipped with a mechanical stirrer, nitrogen inlet, and a condenser. The flask was immersed in a constant temperature bath at 80° C. and heated for 30 mins with nitrogen purging through. 0.9 g of 10% sodium persulfate was added. 5 mins later, monomer solution comprising 6.69 g(0.015 mole) of UV monomer IM-3, 1.923 g(0.015 mole) of butyl acrylate, and 60 mL of N,N-dimethylformamide was feeded into reactor over four hours. Cofeed solution comprising 0.73 g of Igepon T-33, 0.9 g of 10% sodium persulfate, 0.59 g(0.0015 mole) of sodium acrylamido-2-methyl-1-propane sulfonic acid, 0.9 g of sodium bicarbonate and 180 mL water was pumped into the reactor together concurrently. The polymerization was continued for overnight. The latex was cooled, filtered, dialyzed, and concentrated to 5.27% solid with Amicon's Ultrafiltration unit. The Z-average particle size measured by Malvern's Autosizer IIC was 87 nm. The elemental analysis confirmed the composition.

Comparative C-1

This is a conventional dispersion composed of Tinuvin 328 (0.85), Tinuvin 326 (0.15) (from Ciba-Geigy), 1,4-cyclohexylenedimethylene bis(2-ethylhexanoate)(0.33), 2,5-bis(1,1,3,3-tetramethlbutyl)-1,4-benzenediol (0,114), 10% Alkanol LC (0,555), and TCG2 Gel (0.708). The numbers inside the parenthesis are the relative weight ratio. The dispersion was prepared by the colloid mill process in the presence of gelatin as known in the art. Average particle size is 273 nm.

TINUVIN 328

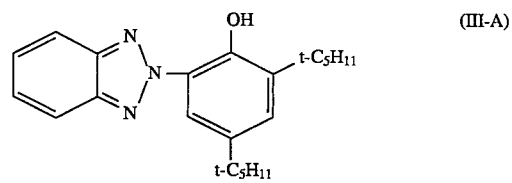

TINUVIN 326

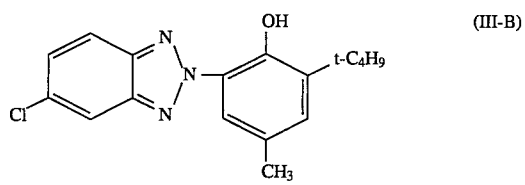

All the polymers were synthesized by the same procedure as described for synthesis of polymers IP-1 and IP-2 except the listed UV absorbing monomers and comonomers were used. The structural formula for UV absorbing monomers have already been described.

TABLE 1

| Sample No. | UV Polymer Compositions | Molar Ratio | Remark |
|---|---|---|---|
| C-1 | III-A & III-B | 85/15 | Comparison |
| CP-1 | CM-1:Ba | 1:1 | Comparison |
| CP-2 | CM-2:Ba:NaAMPS | 1:1:0.1 | Comparison |
| IP-1 | IM-1:Ba:NaAMPS | 1:1:0.1 | Invention |
| IP-2 | IM-3:Ba:NaAMPS | 1:1:0.1 | Invention | where, Ba=Butyl acrylate; and NaAMPS=sodium acrylamido-2-methyl-l-propane sulfonic acid.

Photographic Examples

EXAMPLE 1

The intrinsic light stability of UV absorbing agents themselves is very important for the protection of photographic materials from dye fade. The light stability of the polymeric UV absorbing agents incorporated in photographic elements of this invention was evaluated in comparison to photographic elements using comparative UV absorbing compounds. The coating format for comparative compositions as well as inventive compositions was as follows:

| Gel | 1.35 g/m$^2$ |
|---|---|
| BVSME* | 1.75% by weight of total gel |
| Gel | 1.40 g/m$^2$ |
| UV Absorbing Agent | 2.16 mmole/m$^2$ |
| ///////Cellulose Triacetate Film Support/////////// | |

*BVSME - Bis (vinylsulfonyl methyl) ether.

Figure 2:
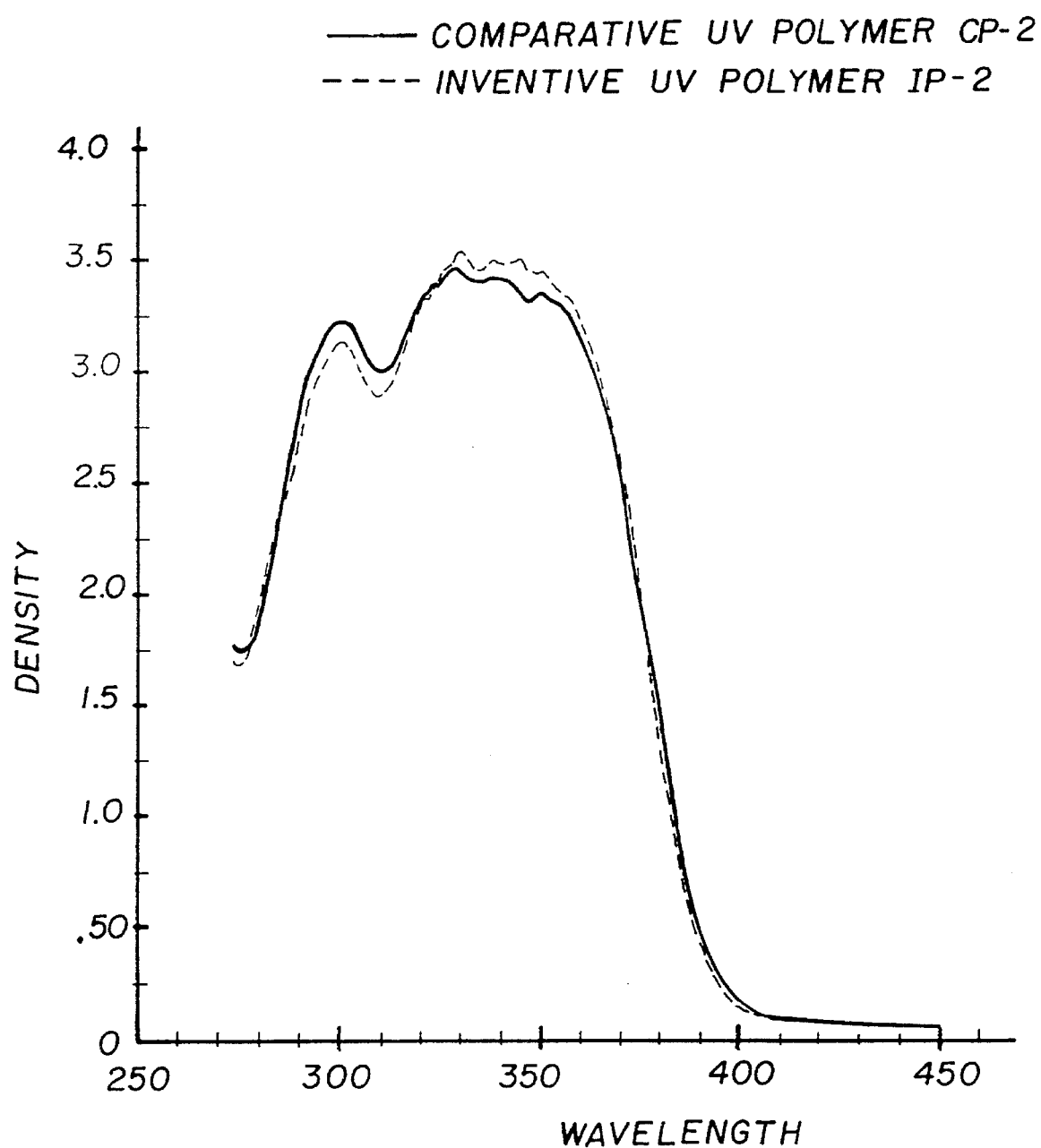
FIG. 2 represents fresh coated absorption spectra of UV absorbing polymers, CP-2 (comparative) and IP-2 (invention).

FIGS. 1 and 2 show the fresh coated absorption spectra of the polymers CP-1, IP-1, CP-2 and IP-2 in the above format. FIG. 1 illustrates that UV absorbing polymer IP-1 of the present invention offers sharper drop-off on the longer wavelength side of the absorption spectrum with a favorable bathochromic tilt of the taller region of the curve. This feature of the present invention offers improved photographic performance. FIG. 2 illustrates that if there is a sterically hindering substituent at 5'-position in the phenyl ring such as 5'-chloro, the spectra of Comparative CP-2 and Inventive IP-2 are almost superimposable. However, free sec-OH group present in CP-2 can result in decreased intrinsic light stabilty, increased light-induced yellowing, poor image keeping and poor raw stock keeping.

The light stability of the above coatings was evaluated using the typical Xenon fadeometer exposure with Xe arc lamp as a light source at 25° C. for four weeks. The samples were irradiated at a distance such that irradiance on the sample was 50 Klux Daylight (280–700 nm) (known as HIS test). The UV absorption spectrum of each sample was taken both before and after irradiation, and the % loss of the absorbance at 360 nm was used as an index of light stability. (For HID and HIS explanations, see Lewis R. Koller, Ultraviolet Radiation, John Wiley & Sons, Inc., N.Y., New York, 1965). The results are shown in Table 2.

TABLE 2

| | Intrinsic Light Stability of UV Absorbers | |
|---|---|---|
| Sample No. | % Loss at 360 nm | Remark |
| CP-1 | 16.00 | Comparison |
| CP-2 | 24.00 | Comparison |
| IP-1 | 9.00 | Invention |
| IP-2 | 5.00 | Invention |

Table 2 demonstrates that photographic elements of this invention incorporating polymeric UV absorbers having repeating units formed from monomers of formula (II), such as IP-1 and IP-2, have much better light stability over the corresponding comparative examples CP-1 and CP-2 respectively. CP-1 and CP-2 have free secondary —OH subsituent on the polymerizable side chain (versus the invention IP-1 and IP-2 which have a blocked —OH substituent on the polymerizable side chain).

EXAMPLE 2

(a) Fresh blue Dmin density and light induced yellowing density

Photographic elements were contstructed as follows:

| Layer No. | Layer Name | Ingredients g/m$^2$ unless otherwise indicated | |
|---|---|---|---|
| 8 | Protective Layer | 1.35 | Gelatin |
| | | BVSME @ 1.75% by weight of total gelatin laydown | |
| 7 | UV Layer | 1.40 | Gelatin |
| | | 2.16 | mmole UV absorber |
| 6 | Interlayer | 0.0216 | Scavenger 1 |
| | | 1.08 | Gel |
| 5 | Cyan Layer | 1.08 | Gelatin |
| | | 0.424 | Cyan Coupler |
| | | 0.00583 | Scavenger 1 |
| | | 0.180 | Red Sensitized AgCl Emulsion |
| | | 0.232 | Coupler Solvent |
| 4 | interlayer | 0.702 | Gelatin |
| | | 0.0434 | Scavenger 1 |
| 3 | Magenta Layer | 1.24 | Gelatin |
| | | 0.390 | Magenta Coupler |
| | | 0.207 | Magenta Stabilizer |
| | | 0.286 | Green Sensitized AgCl Emulsion |
| | | 0.154 | Coupler Solvent |
| 2 | Interlayer | 0.756 | Gelatin |
| | | 0.0945 | Scavenger 1 |
| 1 | Yellow Layer | 1.51 | Gelatin |
| | | 0.735 | Yellow Coupler |
| | | 0.255 | Blue Sensitized AgCl Emulsion |
| | | 0.00950 | Scavenger 2 |
| Support | Sublayer 1 | Resin Coat: Titanox and Optical Brightener Dispersed in polyethylene | |
| | Sublayer 2 | Paper | |
| | Sublayer 3 | Resin Coat: Polyethylene | |

Experiments were conducted on storage stability and absorption characteristics, as well as on light-induced discoloration of color forming dyes and the density at the unexposed area (that is, fresh Dmin). Elements of the present invention incorporating polymeric UV absorbers of formula (II), as well as elements incorporating the comparative UV absorber compositions, were tested.

All couplers, scavenger, and image stabilizers are codispersed in di-butyl phthalate (Coupler Solvent) by the conventional colloidal milled process. The structures of the foregoing are as follows:

MAGENTA COUPLER
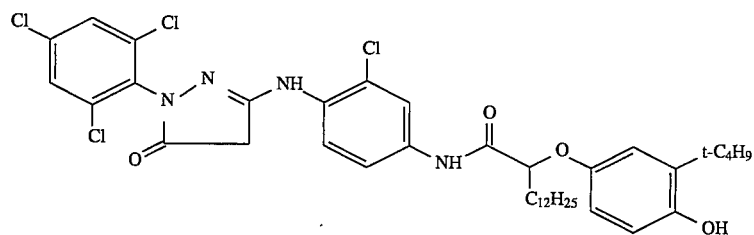
YELLOW COUPLER
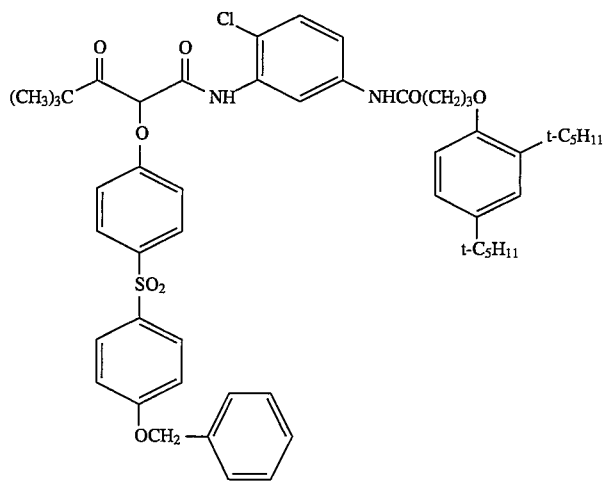
CYAN COUPLER
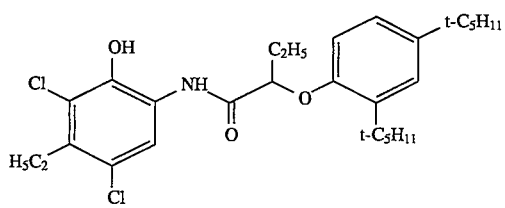
SCAVENGER 1
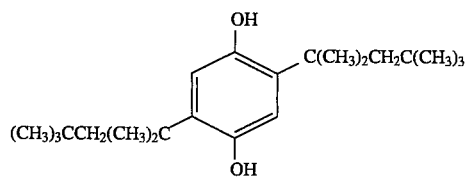
SCAVENGER 2
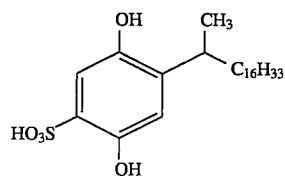

STABILIZER

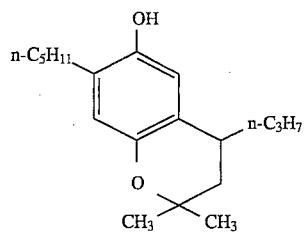

Photographic elements with the above layer structure were exposed with a step tablet wedge to three different colors (red, green, blue) on a sensitometer and subsequently processed by the RA-4 process to provide cyan, magenta, and yellow colors. The photographic papers with the arrangement described above were processed by the well-known RA-4 process (see *Research Disclosure I*, p. 933). Fresh minimum density ("Dmin") of the samples was then measured. The exposed and processed samples were subjected to a fading test with a Xenon lamp with filtered glass (50Klux), as described in Example 1. Fresh Dmin and the amount of light induced yellowing ("Dmin increases from 4-weeks HIS test") were measured in relation to C-1 (C-1 taken as 0) and the results are shown in Table 3 below. Fresh Dmin provided by inventive polymers IP-1 and IP-2 is nearly equivalent to that observed with comparative C-1 and is not of a concern. Particularly, the amount of light induced yellowing was significantly reduced in the elements containing inventive polymers IP-1 and IP-2 versus those containing comparative polymers CP-1 and CP-2. This reduction in light induced yellowing is a major advantage of the photographic elements of the present invention.

TABLE 3

| Sample No. | Fresh Blue Dmin increases compared to C-1 | Blue Dmin increases from 4-weeks HIS test compared to C-1 | Remarks |
| --- | --- | --- | --- |
| C-1 | 0 | 0 | Comparison |
| CP-1 | 0.006 | +0.005 | Comparison |
| CP-2 | 0.021 | +0.001 | Comparison |
| IP-1 | 0.004 | −0.030 | Invention |
| IP-2 | 0.006 | −0.045 | Invention |

Lower Fresh blue Dmin and blue Dmin increases from 4-weeks HIS test are advantageous. Table-3 clearly illustrates the advantages in both important photographic properties of inventive polymeric UV absorbers IP-1 and IP-2 of repeating units of the type of formula (II) over the corresponding comparative polymers CP-1 and CP-2. These data indicate that protection of secondary alcoholic group in the polymerizable chain of the UV monomers of formula (IX) improves the performance of photographic elements.

EXAMPLE 3

(b) Image Keeping and Raw Stock Keeping

Samples were also prepared in the coating format shown below.

| Layer No. | Layer Name | Ingredients g/m² unless otherwise indicated | |
| --- | --- | --- | --- |
| 4 | Protective Layer | 1.3455 | Gelatin |
| | | | BVSME @ 1.75% by weight of total gelatin laydown |
| 3 | UV Layer | 1.40 | Gelatin |
| | | 2.153 mmole | UV Absorber |
| 2 | Magenta Layer | 1.2379 | Gelatin |
| | | 0.3890 | Magenta Coupler |
| | | 0.2067 | Magenta Stabilizer |
| | | 0.2869 | Green Sensitized AgCl Emulsion |
| | | 0.1534 | Coupler Solvent |
| 1 | Gel pad | 3.2293 | Gelatin |
| Support | Sublayer 1 | | Resin Coat: Titanox and Optical Brightener Dispersed in Polyethylene |
| | Sublayer 2 | | Paper |
| | Sublayer 3 | | Resin Coat: Polyethylene |

Samples were then incubated in 48.9° C./50% RH condition for four weeks, followed by exposure and RA-4 process. The density increase in the unexposed area (Dmin) compared to the unincubated sample were recorded as the Dmin increase on raw stock keeping (RSK). Another set of samples were exposed and RA-4 processed, and then incubated in 60° C./70% RH dark oven for four weeks and the Dmin was read and compared to the Dmin before oven incubation. The difference is recorded as the Dmin increase on dark image keeping.

TABLE 4

| Sample No. | Blue Dmin increase compared to C-1 (for Image Keeping Test) | Blue Dmin increase compared to C-1 (for Raw Stock Keeping Test) |
| --- | --- | --- |
| CP-2 | +0.012 | +0.013 |
| IP-2 | −0.001 | +0.007 |

Lower Blue Dmin increase compared to C-1 (for Image Keeping Test and for Raw Stock Keeping Test) is advantageous. The example in Table 4 clearly demonstrates these two advantages of the photographic elements of the present invention incorporating the polymeric UV absorbers with repeating units of formula (II) having protected secondary alcoholic group over those polymers such as comparative example CP-2 containing free secondary alcoholic group.

The advantages of photographic elements of the present invention which use polymeric UV absorbers with repeating units of formula (II), are as follows: good light stability; low fresh Dmin, (that is, more whiteness in the unexposed area of photographic paper); low light induced yellowing; and low blue Dmin increases during Image Keeping and Raw Stock Keeping.

The present invention also specifically contemplates multilayer photographic elements as described in *Research Disclosure*, February 1995, Item 37038 (pages 79–115). Particularly contemplated is the use of any polymer which includes units formed from monomers of the structure of formula (II) in such elements. For example, either or both of polymers IP-1 and IP-2 above, may be used as the UV absorbing compound in an overcoat of each of the photographic elements described in detail in Sections XVII through XXII of *Research Disclosure*, February 1995, Item 37038 (pages 79–115).

The invention has been described in detail with particular reference to preferred embodiments, but it will be understood that variations and modifications can be effected within the spirit and scope of the invention.

We claim:

1. A photographic element comprising a light sensitive silver halide and an ultraviolet absorbing polymer which includes units formed from monomers of the structure of formula (II):

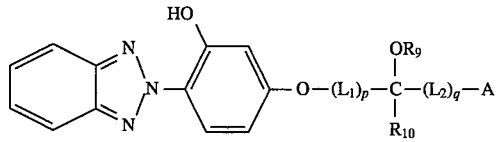

wherein:

p and q are, independently, 0 or 1;

$L_1$ and $L_2$ are bivalent linking groups;

$R_9$ is an acyl group, aryl group or heterocyclyl group;

$R_{10}$ is H, alkyl group, aryl group, or heterocyclyl group;

A is an ethylenically unsaturated polymerizable group; the benzene ring of the benzotriazole and the 2'-hydroxyphenyl ring each may be further substituted or unsubstituted.

2. A photographic element comprising a light sensitive silver halide and an ultraviolet absorbing polymer which includes units of the structure of formula (IIA):

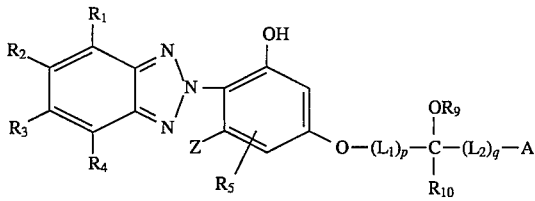

wherein:

p and q are both 1:

$L_1$ and $L_2$ are bivalent linking groups;

$R_1$, $R_2$, $R_3$, $R_4$ and $R_5$ are, independently, H, halogen, cyano, carboxy group, carbamoyl group, sulfoxido group, sulfono group, sufonato group, sulfonamido group, alkyl group, alkoxy group, aryl group, heteroaryl group, aryloxy group, or any two or more of $R_1$ through $R_4$ may together form an alicyclic, aromatic or heteroaromatic group; the phenyl ring of the 2'-hydroxyphenyl ring has no further substituents;

$R_9$ is an acyl group, aryl group or heterocyclyl group;

$R_{10}$ is H, alkyl group, aryl group, or heterocyclyl group;

A is an ethylenically unsaturated polymerizable group; and

Z is H or an OH.

3. A photographic element according to claim 1 wherein $L_1$ is an alkylene group.

4. A photgographic element according to claim 2 wherein the monomers of formula (IIA) are of formula (IIB):

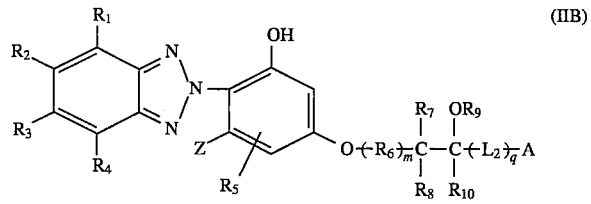

wherein:

$R_6$ is a bivalent linking group;

m is 0 or 1; and $R_7$ and $R_8$ are, independently, H, halogen, alkyl group, or together may form an alicyclic or heteroalicyclic ring.

5. A photographic element according to claim 2 wherein each of $R_1$ through $R_5$ is, independently, an alkyl group, alkoxy group, H or halogen.

6. A photographic element according to claim 2 wherein each of $R_1$ through $R_5$ are, independently, 1 to 20 carbon atom alkyl or alkoxy group, or H or halogen.

7. A photographic element according to claim 5 wherein $R_1$, $R_4$ and $R_5$ are all H.

8. A photographic element according to claim 6 wherein $R_1$, $R_4$ and $R_5$ are all H.

9. A photographic element comprising a light sensitive silver halide and an ultraviolet absorbing polymer which includes units of formula (IIC):

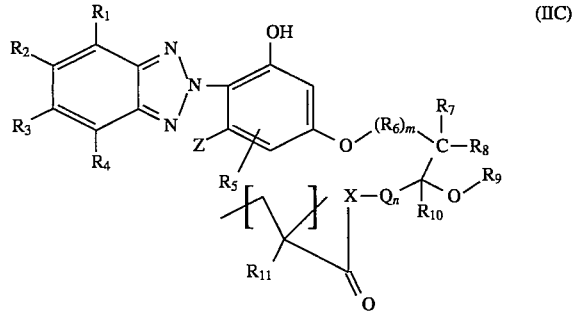

wherein:

$R_1$, $R_2$, $R_3$, $R_4$ and $R_5$ are, independently, H, halogen, cyano, carboxy group, carbamoyl group, sulfoxido group, sulfono group, sulfonato group, sulfonomido group, alkyl group, alkoxy group, aryl group, heteroaryl group, aryloxy group, or any two or more of $R_1$ through $R_4$ may together form an alicyclic, aromatic or heteroaromatic group; the 2'-hydroxyphenyl ring has no further substituents;

$R_6$ is a bivalent linking group;

$R_7$ and $R_8$ are, independently, H, halogen, alkyl group, or together may form an alicyclic or heteroalicyclic ring;

$R_9$ is an acyl group, alkyl group, aryl group, or heterocyclyl group;

$R_{10}$ is H, alkyl group, aryl group, or heterocyclyl group;

Z is H or an OH;

n is an integer from 0 to 6;

each Q is a methylene group;

m is 0 or 1;

X is O or —N(Y)— where Y is H or an alkyl group; and $R_{11}$ is H or an alkyl group.

10. A photographic element according to claim 9 wherein $R_1$, $R_4$ and $R_5$ are H.

11. A photographic element according to claim 9 wherein $R_6$ is an alkylene group.

12. A photographic element according to claim 10 wherein m is 0, Q is a methylene group, X is O, and $R_{11}$ is H or a 1 to 6 carbon atom alkyl group.

13. A photographic element according to claim 12 wherein $R_2$ is H and $R_3$ is H, chloro, bromo or fluoro.

14. A photographic element according to claim 13 wherein $R_7$, $R_8$ and $R_{10}$ are, independently, H or a 1 to 6 carbon atom alkyl group.

15. A photographic element according to claim 13 wherein $R_7$, $R_8$ and $R_{10}$ are all H.

16. A photographic element according to claim 15 wherein Q is an unsubstituted methylene.

17. A photographic element comprising at least one light sensitive silver halide emulsion layer and a non-light sensitive layer, wherein an ultraviolet absorbing polymer is located in the non-light sensitive layer, said polymer including units formed from monomers of the structure of formula (I):

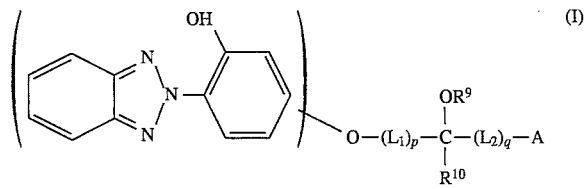

wherein:

p and q are, independently, 0 or 1;

$L_1$ and $L_2$ are bivalent linking groups;

$R_9$ is an acyl group, aryl group or heterocyclyl group;

$R_{10}$ is H, alkyl group, aryl group, or heterocyclyl group;

A is an ethylenically unsaturated polymerizable group; the benzene ring of the benzotriazole and the 2'-hydroxyphenyl ring each may be further substituted or unsubstituted.

18. A photographic element according to claim 17 wherein the non-light sensitive layer containing the ultraviolet absorbing polymer is located above all light sensitive layers.

19. A photographic element comprising at least one gel layer and an ultraviolet absorbing polymer which includes units formed from monomers of the structure of formula (I):

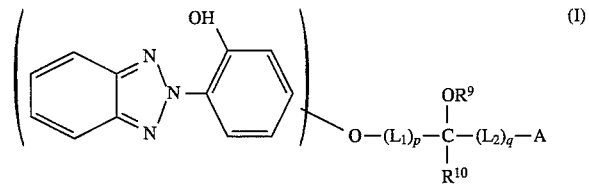

wherein:

p and q are, independently, 0 or 1;

$L_1$ and $L_2$ are bivalent linking groups;

$R_9$ is; an acyl group, aryl group or heterocyclyl group;

$R_{10}$ is H, alkyl group, aryl group, or heterocyclyl group;

A is an ethylenically unsaturated polymerizable group; the benzene ring of the benzotriazole and the 2'-hydroxyphenyl ring each may be further substituted or unsubstituted; and wherein the ultraviolet absorbing polymer is incorporated in the gel layer in the form of a latex.

20. A photographic element according to claim 1 wherein the ratio of monomeric units from formula (IIB) to other monomeric units is between 10:1 to 1:10.

21. A photographic element according to claim 5 wherein the ratio of monomeric units from formula (IIC) to other monomeric units is between 10:1 to 1:10.

22. A photographic element comprising a light sensitive silver halide and an ultraviolet absorbing polymer which includes units formed from monomers of the structure of formula (II):

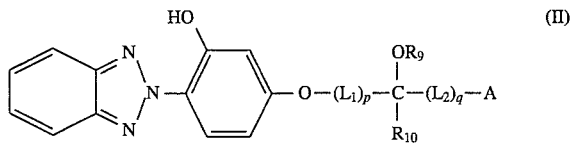

wherein:

p and q are, independently, 0 or 1;

$L_1$ and $L_2$ are bivalent linking groups;

$R_9$ is formyl, carbamyl or alkylsulfonyl;

$R_{10}$ is H, alkyl group, aryl group, or heterocyclyl group;

A is an ethylenically unsaturated polymerizable group; the benzene ring of the benzotriazole and the 2'-hydroxyphenyl ring each may be further substituted or unsubstituted.

23. A photographic element comprising a light sensitive silver halide and an ultraviolet absorbing polymer which includes units of the structure of formula (IIA):

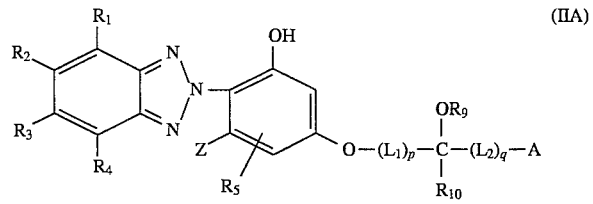

wherein:

p and q are both 1:

$L_1$ and $L_2$ are bivalent linking groups;

$R_1$, $R_2$, $R_3$, $R_4$ and $R_5$ are, independently, H, halogen, cyano, carboxy group, carbamoyl group, sulfoxido group, sulfono group, sufonato group, sulfonamido group, alkyl group, alkoxy group, aryl group, heteroaryl group, or aryloxy group, or any two or more of $R_1$ through $R_4$ may together form an alicyclic, aromatic or heteroaromatic group; the phenyl ring of the 2'-hydroxyphenyl ring has no further substituents;

$R_9$ is formyl, carbamyl or alkylsulfonyl;

$R_{10}$ is H, alkyl group, aryl group, or heterocyclyl group;

A is an ethylenically unsaturated polymerizable group; and

Z is H or an OH.

24. A photgographic element according to claim 23 wherein the monomers of formula (IIA) are of formula (IIB):

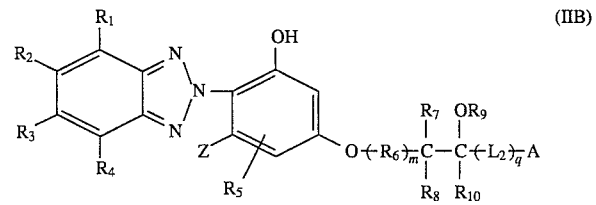

wherein:

$R_6$ is a bivalent linking group;

m is 0 or 1; and $R_7$ and $R_8$ are, independently, H, halogen, alkyl group, or together may form an alicyclic or heteroalicyclic ring.

25. A photographic element according to claim 19 wherein the ultraviolet absorbing polymer is a copolymer.

26. A photographic element according to claim 25 wherein the ultraviolet absorbing polymer is a copolymer having repeating units of either the formula:

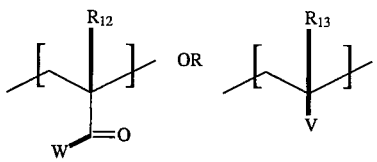

wherein: W is an amino group, alkoxy group, or phenoxy group; V is a phenyl group; and $R_{12}$ and $R_{13}$ are H or a 1 to 6 carbon atom alkyl group.

27. A photographic element according to claim 25 wherein the ratio of monomeric units from formula (I) to other monomeric units is between 10:1 to 1:10.

28. A photographic element according to claim 19 wherein the ultraviolet absorbing polymer is present in the photographic element in an amount of between 0.2 g/m² and 10 g/m².

* * * * *